(12) United States Patent
Limmer et al.

(10) Patent No.: US 11,241,201 B2
(45) Date of Patent: Feb. 8, 2022

(54) COMPRESSION UNIT WITH A U-SHAPED ACCOMMODATING UNIT FOR AN EXCHANGEABLE COMPRESSION ELEMENT

(71) Applicant: Siemens Healthcare GmbH, Erlangen (DE)

(72) Inventors: Andreas Limmer, Fuerth (DE); Helmut Gollwitzer, Erbendorf (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/024,819

(22) Filed: Sep. 18, 2020

(65) Prior Publication Data

US 2021/0093262 A1 Apr. 1, 2021

(30) Foreign Application Priority Data

Sep. 27, 2019 (DE) ...................... 10 2019 214 889.1

(51) Int. Cl.
*A61B 6/04* (2006.01)
*A61B 6/00* (2006.01)

(52) U.S. Cl.
CPC ............ *A61B 6/0414* (2013.01); *A61B 6/502* (2013.01)

(58) Field of Classification Search
CPC ....... A61B 6/0414; A61B 6/502; A61B 6/025; A61B 6/0407; A61B 6/0421; A61B 8/403; A61B 8/4209; A61B 2090/3904
See application file for complete search history.

(56) References Cited

U.S. PATENT DOCUMENTS

2011/0129062 A1 6/2011 Hoernig
2021/0113163 A1* 4/2021 St. Pierre ............... A61B 6/502

FOREIGN PATENT DOCUMENTS

| DE | 102006004667 A1 | 8/2006 |
| DE | 102009056176 A1 | 6/2011 |
| DE | 102014202955 A1 | 8/2015 |
| DE | 102017217086 A1 | 3/2019 |
| DE | 102018201401 A1 | 8/2019 |

* cited by examiner

*Primary Examiner* — Don K Wong
(74) *Attorney, Agent, or Firm* — Harness, Dickey & Pierce, P.L.C.

(57) ABSTRACT

A compression unit is for a mammography system. In an embodiment, the compression unit includes an essentially U-shaped accommodating unit including two opposing fastening elements, connected via an adjustable spacer element arranged between the two opposing fastening elements, a distance between the two opposing fastening elements being adjustable. In an embodiment, the compression unit further includes a compression element, fastenable and exchangeable in the accommodating unit.

20 Claims, 3 Drawing Sheets

COMPRESSION UNIT WITH A U-SHAPED ACCOMMODATING UNIT FOR AN EXCHANGEABLE COMPRESSION ELEMENT

PRIORITY STATEMENT

The present application hereby claims priority under 35 U.S.C. § 119 to German patent application number DE 102019214889.1 filed Sep. 27, 2019, the entire contents of which are hereby incorporated herein by reference.

FIELD

Embodiments of the invention generally relate to a compression unit of a mammography system for compression of the breast during a mammography or a biopsy removal and to a mammography system for this purpose.

BACKGROUND

A mammography system is essentially composed of an X-ray arm which is arranged pivotably on a stand with an X-ray source and a detector unit with an X-ray detector. The surface of the detector unit is designed as a support surface for a breast of a patient to be examined. The X-ray arm and the detector unit can be designed in such a way that they can be moved independently of one another. For better detection of malignant tissue in an X-ray image, the breast to be examined is pressed onto or fixed to the support surface via a compression unit.

A compression unit of a mammography device is known from the publication DE 10 2009 056 176 A1, wherein devices for tensioning at least one compression belt in a first and second fixing unit are arranged on both sides of an object table.

The breast must be clamped and compressed according to the current state of mammography. For this purpose, different compression units, so-called paddles, are used, which are adapted to the size of the breast.

SUMMARY

Hitherto, the problem was solved by inserting various compression units into a holder on the system. These compression units are shaped in such a way that they can absorb the compression force. As a result, however, the inventors recognized that the geometry of these compression units was very complicated and the costs for such compression units were very high.

At least one embodiment of the invention specifies a compression unit and a mammography system which enable various configurations of the compression unit to be provided cost-effectively.

Embodiments of the invention are directed to a compression unit and a mammography system.

At least one embodiment of the invention relates to a compression unit for a mammography system having an accommodating unit and a compression element. The essentially U-shaped accommodating unit comprises two opposing fastening elements which are connected to one another by way of an adjustable spacer element arranged between them, a distance between the fastening elements being adjustable. The compression element can be fastened and exchanged in the accommodating unit. The compression unit can be referred to as a so-called paddle, compression module or compression plate. In particular, the compression unit cannot comprise the lifting mechanism or the adjusting unit for adjusting the compression strength.

At least one embodiment of the invention furthermore relates to a mammography system comprising a compression unit according to at least one embodiment of the invention. The advantages of the compression unit according to at least one embodiment of the invention can be advantageously transferred to the mammography system according to at least one embodiment of the invention.

At least one embodiment of the invention furthermore relates to a compression unit for a mammography system, comprising:

an essentially U-shaped accommodating unit including two opposing fastening elements, connected via an adjustable spacer element arranged between the two opposing fastening elements, a distance between the two opposing fastening elements being adjustable; and a compression element, fastenable and exchangeable in the accommodating unit.

At least one embodiment of the invention furthermore relates to a mammography system, comprising:

an X-ray source;

an X-ray detector; and a compression unit, arranged between the X-ray source and a support surface of the X-ray detector, the compression unit including an essentially U-shaped accommodating unit including two opposing fastening elements, connected via an adjustable spacer element arranged between the two opposing fastening elements, a distance between the two opposing fastening elements being adjustable; and a compression element, fastenable and exchangeable in the accommodating unit.

BRIEF DESCRIPTION OF THE DRAWINGS

Hereinafter example embodiments of the invention are explained in more detail with reference to the drawings, in which.

DETAILED DESCRIPTION OF THE EXAMPLE EMBODIMENTS

Figure 1:
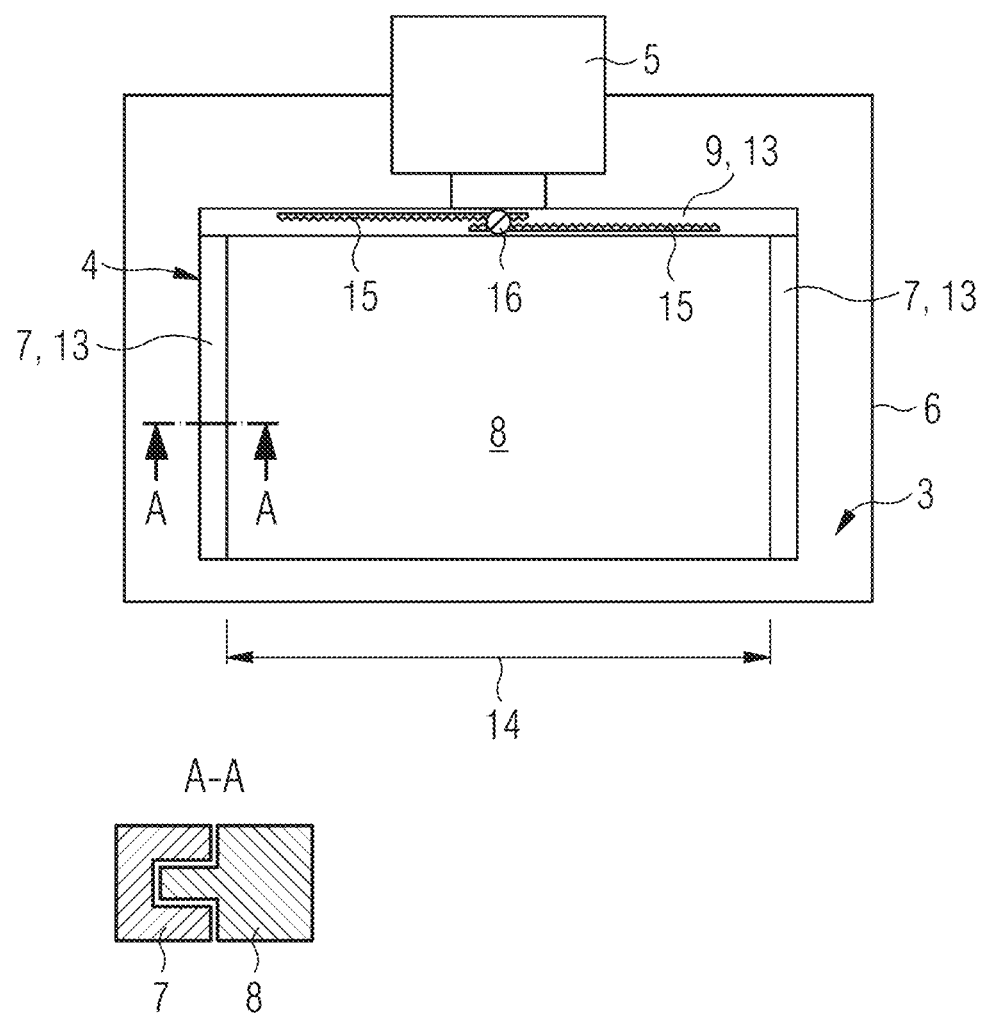
FIG. 1 shows a schematic representation of a compression unit according to an embodiment of the invention.

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the invention relates to a compression unit for a mammography system having an accommodating unit and a compression element. The essentially U-shaped accommodating unit comprises two opposing fastening elements which are connected to one another by way of an adjustable spacer element arranged between them, a distance between the fastening elements being adjustable. The compression element can be fastened and exchanged in the accommodating unit. The compression unit can be referred to as a so-called paddle, compression module or compression plate. In particular, the compression unit cannot comprise the lifting mechanism or the adjusting unit for adjusting the compression strength.

The spacer element can be designed as one element. The spacer element can be designed in one piece as a structural unit. Alternatively, the spacer element can be designed in two pieces, it being possible for there to be a distance between the two parts of the spacer elements. The spacer element can comprise telescopic kinematics for adjusting the distance. The distance can be adjusted via a spindle drive or a tooth system, for example having a rack and a pinion.

The two fastening elements can be referred to as clasps. By way of the two fastening elements accommodating and clamping the compression plate or the compression element, the breast can be compressed. Compression can be produced between the surface of the detector unit as the support surface of the breast and the compression element by setting the compression element at a distance from the support surface corresponding to the compression strength or compression pressure.

The fastening elements can be opened and closed to obtain different sizes of compression plates or different distances. These clasps enable very simple plates to be formed and provided. The force is absorbed by the clasps.

The accommodation of the compression element and the transmission of force to produce the compression is advantageously made possible by way of the fastening elements. These fastening elements can remain on the mammography system. Advantageously, the compression element is exchangeable. Advantageously, various compression elements can be used in conjunction with the fastening elements. Advantageously, the design of the compression element can be simple as the main function of transmitting force takes place by way of the fastening elements.

According to one embodiment of the invention, the fastening of the compression element in the accommodating unit is formed via a slot and key system, a magnetic connection system or a push-button system. For example, the compression element is inserted into the fastening elements by way of a T-slot or the like. The slot can in particular be formed on the fastening elements. The slot can preferably be formed on the opposing inner sides of the fastening element. The basic shape of the fastening elements can be angular for example, the slot being incorporated into this basic shape. The compression element can, for example, correspondingly comprise the key. In particular, slot and key can be designed in a form-fitting manner. A T-slot and key system is particularly advantageous.

In a further embodiment of the invention, the fastening of the compression element in the accommodating unit can be formed via a push-button system. A push-button element can be formed on a side of the fastening element and the counterpart of the push-button element can be formed on the compression element. Particularly preferably, a push-button system can be formed in conjunction with a compression element comprising a fabric. Advantageously, the fastening can be designed to be easily detachable.

Alternatively, a magnetic connection system may be formed. For this purpose, for example, the fastening elements can have a metal at least on one side, for example the underside, which is in particular ferromagnetic. The metal can be iron, for example. The upper side of the compression element can have at least partially magnetic elements on the contact surfaces so that the compression element can be fastened to the fastening elements from below by way of the magnetic elements. This embodiment can be provided in particular for plate-shaped, preferably reusable, compression elements. The compression force can further increase the stability. Furthermore, a locking mechanism can be provided so that the compression element is safely and securely connected to the fastening element in a detachable manner.

Advantageously, the compression element can be connected simply and quickly to the fastening elements in a detachable and stable manner. Various fastening systems can be formed. For example, these can be combined or alternatively used in the examination. For example, a push-button system can be designed as a locking mechanism in addition to a magnetic connection system.

According to one embodiment of the invention, a compression element from a selection of different shapes and/or different sizes can be fastened in the accommodating unit. The shape can, in particular, be rectangular, essentially flat, and planar. Alternatively, a curved or flexible shape or curved or flexible compression elements can also be used. A recess can be provided in the compression element, for example, in order to perform a biopsy on the breast under compression.

The size of the, in particular various, compression elements may vary, in particular parallel to the longitudinal axis of the spacer element. Alternatively, or additionally, the size of the, in particular various, compression elements may vary, in particular parallel to the longitudinal axis of the fastening element. The size may refer to an extension. The compression unit can be advantageously adapted to the type of examination and/or breast size.

According to one embodiment of the invention, the compression element is a plate. The compression element can in particular be rectangular, essentially flat, and planar. The compression element has a material which is as homogeneous and X-ray-permeable as possible. As a material, the compression element may comprise, for example, a plastic, in particular PMMA or the like. Advantageously, a sufficiently large compression force can act on the breast by way of the compression unit. Advantageously, the compression unit can have a particularly good level of stability.

According to one embodiment of the invention, the compression element comprises a fabric or a gauze or a film. By opening and closing the fastening elements, a fabric or mesh, in particular a gauze, or a film can be used, which is tensioned by opening the fastening elements. As a result, the compression elements are advantageously simple to design. Advantageously, the compression element can adapt particularly well to the shape and size of the breast. Advantageously, compression can also be maintained while using an additional ultrasound recording. Advantageously, the fabric or the film can be pierced by the biopsy needle, compression being retained.

According to one embodiment of the invention, the fabric or the gauze or the film is fastened to opposing holding elements, wherein the holding elements each interact with the fastening elements as a connection. The compression element can be connected to the fastening elements by way of holding elements in the form of, for example, plastic counterparts. The compression element is inserted into the fastening elements, for example, by way of a T-slot or the like. The slot can be formed, in particular, on the fastening elements, for example as a holding element in the form of a plastic counterpart. The slot can preferably be formed on the opposing inner sides of the fastening elements. The slot and key system for plate-shaped compression elements and compression elements comprising a fabric or a film can be used in a particularly advantageous manner. The fabric or the film can be tensioned by way of the method of fastening elements.

The fabric or the film can be tensioned between holding elements and/or fastening elements. In one embodiment, rolled-up fabric or rolled-up film can be held on at least one holding element or on at least one fastening element. The rolled-up fabric or the rolled-up film can be used as a reserve for successive examinations, one part in each case being pulled out and tensioned according to the required dimensions and this part being detached after the examination and, if appropriate, disposed of. The roll-up mechanism on the holding element or on the fastening element can be used to tension the fabric or the film. Tensioning the fabric or the film is usually necessary to achieve sufficient compression. The compression element comprising the fabric or the film can be referred to as a so-called "compression belt". Advantageously, adequate compression can be achieved using a fabric or a film as a compression element.

According to one embodiment of the invention, the spacer element is designed as a tensioning apparatus for the fabric or the gauze or the film. Alternatively, or additionally, the fabric or the film can be tensioned by moving the fastening element apart or by way of increased distancing of the fastening element. The adjustment of the distance on the spacer element can be used for tensioning the fabric or the film. In particular, the fabric or the film can be fixed to the holding elements or the fastening elements so that tensioning of the fabric or the film is advantageously made possible via selection of the distance. The compression element can be fastened to the fastening element at a first, in particular smaller, distance by way of the holding elements. The distance can be changed to a second, in particular greater, distance, the fabric or the film being tensioned. The second distance can be predefined. Alternatively, the second distance can be specific to the patient or examination.

According to one embodiment of the invention, the compression element can be used once. The compression elements can be manufactured and designed as disposable articles or articles for one-off use. Cleaning can be advantageously dispensed with after the examination. In particular, the compression unit can comprise a fabric or a film as an article for one-off use. In particular, after an additional ultrasound examination, the fabric or the gauze can be disposed of while maintaining the compression. Advantageously, removal of the ultrasonic contact gel from the fabric can be avoided.

According to one embodiment of the invention, the distance is manually adjustable. Advantageously, gentle manual compression can be made possible. The spacer element can be opened and closed by a motor or manually.

According to one embodiment of the invention, the distance can be adjusted by a motor. A motor element in the form of an electric motor can be provided on the spacer element. The motor element can be controlled via a control unit. For example, the rough or fine adjustment of the distance can be performed by a motor. The fine or rough adjustment of the distance can be performed manually.

According to one embodiment of the invention, the fastening elements are symmetrically adjustable with respect to a predetermined reference point of the spacer element. The reference point may, for example, be a center point of the spacer element. The opening and closing of the spacer element can take place symmetrically.

According to one embodiment of the invention, the fastening elements are asymmetrically adjustable with respect to a predetermined reference point of the spacer element.

The opening and closing of the spacer element can take place asymmetrically in order to realize a so-called shift function. The shift function can be advantageously used without a compression unit specially designed for this purpose as the shift or lateral displacement can be adjusted individually or in an examination-specific manner by way of the spacer element.

According to one embodiment of the invention, the compression element is L-shaped in cross-section so that a contact surface arranged essentially at right angles is formed on the compression element for contact with the chest of the patient. The contact surface can in particular be adaptable to the patient, for example by using a malleable material at least for the contact surface. Particularly advantageously, the fastening elements can also be L-shaped in design. For example, a fabric or a film can be used with the L-shaped fastening elements. Patient comfort can be advantageously increased.

At least one embodiment of the invention furthermore relates to a mammography system comprising a compression unit according to at least one embodiment of the invention. The advantages of the compression unit according to at least one embodiment of the invention can be advantageously transferred to the mammography system according to at least one embodiment of the invention.

Advantageously, the costs for compression units as accessories can be reduced. Advantageously, the mammography system can be easily adapted to different types of examination. Advantageously, patient comfort can be increased. Advantageously, improved, patient-specific compression can be made possible.

FIG. 1 shows an example embodiment of the compression unit 4 according to the invention for a mammography system. The compression unit 4 has an essentially U-shaped accommodating unit 13 comprising two opposing fastening elements 7 which are connected to one another by way of an adjustable spacer element 9 arranged between them, a distance between the fastening elements being adjustable. The distance 14 can be adjusted via a spindle drive (not shown) or a tooth system, for example having racks 15 and a pinion 16 arranged between them, or alternatively, one pinion 16 per rack 15. The distance can be adjusted manually or via a motor. The fastening elements 7 are symmetrically adjustable with respect to a predetermined reference point of the spacer element 9, in particular, the center point or the fastening point on the adjusting unit 5. Alternatively, the fastening elements 7 can be symmetrically adjusted with respect to a predetermined reference point of the spacer element 9.

The compression unit 4 has a compression element 8 which can be fastened and exchanged in the accommodating unit 13. The compression unit 4 is fastened to the adjusting unit 5, which serves to adjust the compression strength between the compression unit 4 and the support surface 3 of the X-ray detector 6.

The fastening of the compression element 8 in the accommodating unit 13 is formed by way of a slot and key system (see sectional view A-A). Alternatively, the fastening can be formed by way of a magnetic connection system or a push-button system (not shown). A compression element 8 from a selection of different shapes and/or different sizes can be fastened in the accommodating unit 13.

Figure 2:
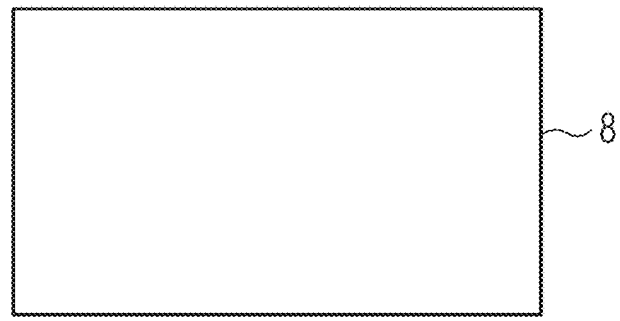
FIG. 2 shows a schematic representation of a plate-shaped compression element.

FIG. 2 shows an example embodiment of the plate-shaped compression element 8. The compression element 8 is a plate, preferably made of a plastic material.

Figure 3:
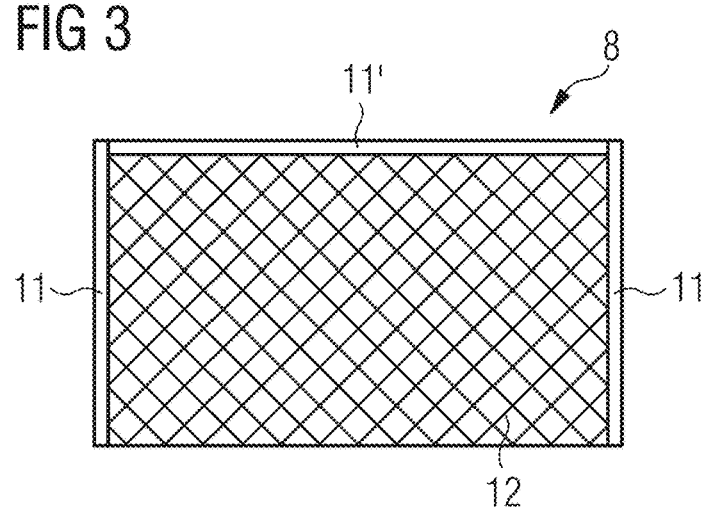
FIG. 3 shows a schematic representation of a compression element comprising a fabric.

FIG. 3 shows an example embodiment of a compression element 8 comprising a fabric 12. In an alternative embodiment, a film can be used instead of the fabric 12. The compression element comprises a fabric 12, for example in the form of a gauze. The fabric 12 or the gauze are fastened to opposing holding elements 11 and the holding elements 11 in each case interact with the fastening elements as a connection to the accommodating unit. An additional holding element 11' can be provided between the holding elements 11, which in the fastened state is directed towards the adjusting unit or towards the patient. The holding element 11 and the additional holding element 11' form a three-sided frame for the fabric 12. The spacer element can be designed as a tensioning apparatus for the fabric 12 or the gauze.

Figure 4:
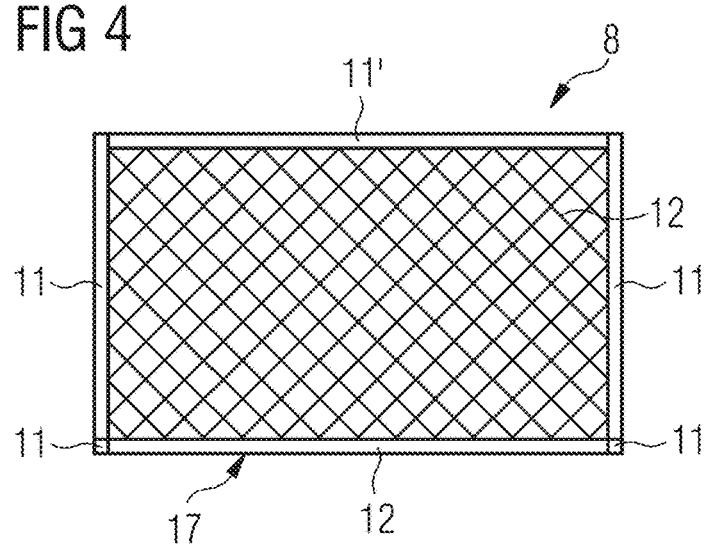
FIG. 4 shows a schematic representation of a compression element with an L-shaped cross-section in plan view.

FIG. 4 shows an example embodiment of a compression element 8 with an L-shaped cross-section in plan view. The compression element 8 is L-shaped in cross-section so that a contact surface 17 arranged essentially at right angles is formed on the compression element 8 for contact with the chest of the patient.

Figure 5:
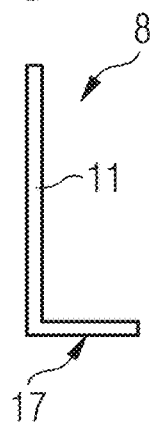
FIG. 5 shows a schematic representation of a compression element with an L-shaped cross-section in side view.

FIG. 5 shows an example embodiment of a compression element 8 with an L-shaped cross-section in side view. In particular, the fastening elements 11 are L-shaped in design.

Figure 6:
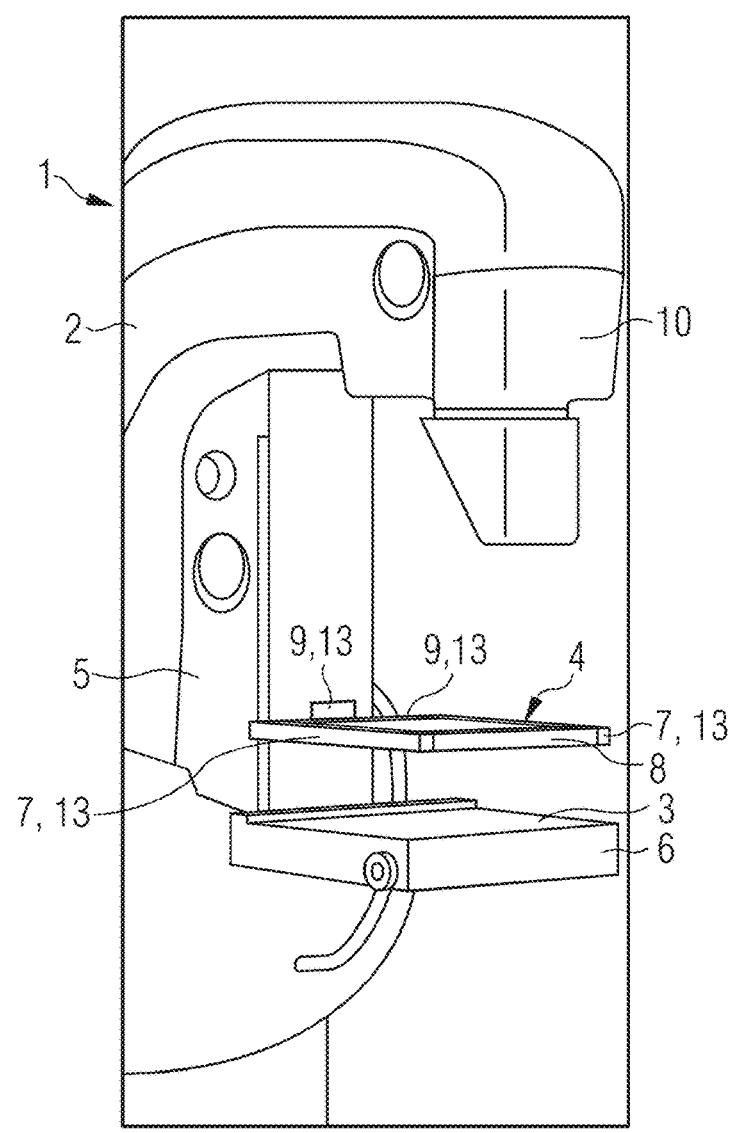
FIG. 6 shows a schematic representation of a mammography system according to an embodiment of the invention.

FIG. 6 shows an example embodiment of a mammography system 1 according to the invention. The mammography system 1 according to the invention has an X-ray arm 2 with an X-ray source 10. The mammography system 1 has an adjusting unit 5 for the compression unit 4. The compression unit 4 is fastened to the adjusting unit 5. The compression unit 4 is arranged between the X-ray source 10 and the support surface 3 of the X-ray detector 3. By way of the adjusting unit, a distance between the compression unit 4 and the support surface 3 can be adjusted so that a breast arranged between them can be compressed.

Although the invention was illustrated in more detail by the preferred example embodiment, the invention is not limited by the disclosed examples, and other variations may be derived therefrom by a person skilled in the art without departing from the scope of the invention.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A compression unit for a mammography system, comprising:
an essentially U-shaped accommodating unit including two opposing fastening elements, connected via an adjustable spacer element arranged between the two opposing fastening elements, a distance between the two opposing fastening elements being adjustable; and
a compression element, fastenable and exchangeable in the accommodating unit.

2. The compression unit of claim 1, wherein the compression element is fastenable in the essentially U-shaped accommodating unit via a slot and key system, a magnetic connection system or a push-button system.

3. The compression unit of claim 1, wherein a compression element, of at least one of different shapes and different sizes, is fastenable in the accommodating unit.

4. The compression unit of claim 1, wherein the compression element is a plate.

5. The compression unit of claim 1, wherein the compression element includes a fabric, a gauze or a film.

6. The compression unit of claim 5, wherein the fabric, the gauze or the film is fastened to opposing holding elements, and wherein the opposing holding elements each interact with the two opposing fastening elements as a connection.

7. The compression unit of claim 5, wherein the spacer element is designed as a tensioning apparatus for the fabric, the gauze, or the film.

8. The compression unit of claim 1, wherein the compression element is usable once.

9. The compression unit of claim 1, wherein the distance is manually adjustable.

10. The compression unit of claim 1, wherein the distance is adjustable via a motor.

11. The compression unit of claim 1, wherein the two opposing fastening elements are symmetrically adjustable with respect to a reference point of the spacer element.

12. The compression unit of claim 1, wherein the two opposing fastening elements are asymmetrically adjustable with respect to a reference point of the spacer element.

13. The compression unit of claim 1, wherein the compression element is L-shaped in cross-section, a contact surface, arranged essentially at right angles, being formed on the compression element for contact with a chest of the patient.

14. A mammography system comprising compression unit of claim 1.

15. The compression unit of claim 1, wherein a compression element, of at least one of different shapes and different sizes, is fastenable in the accommodating unit.

16. The compression unit of claim 1, wherein the compression element is a plate.

17. The compression unit of claim 1, wherein the compression element includes a fabric, a gauze or a film.

18. The compression unit of claim 5, wherein the fabric, the gauze or the film is fastened to opposing holding elements, and wherein the opposing holding elements each interact with the fastening elements as a connection.

19. A mammography system, comprising:
an X-ray source;
an X-ray detector; and
a compression unit, arranged between the X-ray source and a support surface of the X-ray detector, the compression unit including
an essentially U-shaped accommodating unit including two opposing fastening elements, connected via an adjustable spacer element arranged between the two opposing fastening elements, a distance between the two opposing fastening elements being adjustable; and
a compression element, fastenable and exchangeable in the accommodating unit.

20. The mammography system of claim 19, wherein the compression element is fastenable in the essentially U-shaped accommodating unit via a slot and key system, a magnetic connection system or a push-button system.

* * * * *